United States Patent [19]

Shen

[11] Patent Number: 4,547,589

[45] Date of Patent: Oct. 15, 1985

[54] HYDROLYSIS OF NITRILOTRIACETONITRILE

[75] Inventor: Chung Y. Shen, St. Louis, Mo.

[73] Assignee: Monsanto Company, St. Louis, Mo.

[21] Appl. No.: 567,583

[22] Filed: Jan. 3, 1984

[51] Int. Cl.$^4$ ............................................ C07C 101/20
[52] U.S. Cl. ................................... 562/572; 562/554
[58] Field of Search ................................. 562/572, 554

[56] References Cited

U.S. PATENT DOCUMENTS

| | | | |
|---|---|---|---|
| 3,183,262 | 5/1965 | Singer | 562/572 |
| 3,393,234 | 7/1968 | Wollensak | 562/572 |
| 3,409,666 | 11/1968 | Foreman | 562/572 |
| 3,715,393 | 2/1973 | Ribaldone | 562/572 |
| 3,772,374 | 11/1973 | Shen | 562/572 |
| 3,917,685 | 11/1975 | Bergeron | 562/572 |
| 3,956,379 | 5/1976 | Beaver | 562/554 |

Primary Examiner—Michael L. Shippen
Attorney, Agent, or Firm—Raymond C. Loyer; J. C. Logomasini; A. H. Cole

[57] ABSTRACT

A process for producing nitrilotriacetate salts from nitrilotriacetonitrile in which a mixture of substantially stoichiometric amounts of an alkali metal hydroxide and nitrilotriacetonitrile in water are partially hydrolyzed, followed by boiling to complete the reaction, followed by addition of a bleaching agent, and recovery of the product as a solution or in crystalline form.

22 Claims, No Drawings

HYDROLYSIS OF NITRILOTRIACETONITRILE

FIELD OF THE INVENTION

This invention relates to a process for converting nitrilotriacetonitrile to nitrilotriacetate salts.

BACKGROUND

Salts of nitrilotriacetate are useful and well known as detergent builders. They are normally prepared by hydrolysis of nitrilotriacetonitrile. Nitrilotriacetonitrile is also well known, and can be prepared from ammonia or an ammonium salt, formaldehyde, and hydrogen cyanide, or from hexamethylenetetramine, formaldehyde and hydrogen cyanide.

Nitrilotriacetonitrile is hydrolyzed to form a nitrilotriacetate salt according to chemical equations such as the following:

$$N(CH_2CN)_3 + 3NaOH + 3H_2O \rightarrow N(CH_2COONa)_3 + 3NH_3$$

This reaction can also be accomplished using hydroxides of other alkali metals. The product can be isolated as crystals of the monohydrate, or can be sold as a solution, usually about 40%, in water.

The nitrilotriacetate salt must be substantially colorless to be useful commercially as a detergent builder. It is preferred that a 40% solution of the nitrilotriacetate salt in water have an APHA color no greater than 100, or more preferably no greater than 50. The standard method of meeting the color requirements of the product is utilization of excess hydroxide. Excess hydroxide is known to reduce color formation in the nitrilotriacetate product. But, the excess hydroxide must be removed from the product, such as by a separation of the crystallized product from the mother liquor containing the excess hydroxide. This mother liquor must either be disposed of or recycled. Because of the extra steps associated with the use of excess hydroxide, a process to produce low color nitrilotriacetate salts using stoichiometric hydroxide would be an advancement in the art.

Commercially useful nitrilotriacetate salts, whether sold as crystalline material, or as a solution, must be of high purity, and must not contain appreciable levels of undesirable impurities, such as cyanide. Additionally, a commercial process should produce this product in as simple and straightforward a manner as possible, and with minimal capital and energy requirements. This invention meets these objectives in the following manner.

SUMMARY OF THE INVENTION

This invention provides a process for production of a nitrilotriacetate salt, comprising:

a. partially hydrolyzing a mixture of substantially stoichiometric amounts of nitrilotriacetonitrile and an alkali metal hydroxide in water, at a temperature from about 25° C. to about 85° C.;

b. boiling said partially hydrolyzed mixture for at least about 30 minutes; and c. adding from at least about 0.04% by weight of the mixture of a bleaching agent, such as hydrogen peroxide.

The product can then either be isolated as crystalline nitrilotriacetate salt by a conventional means such as crystallization or spray drying, or the reaction mixture can be concentrated or diluted with water to produce a commercially marketable solution.

DETAILED DESCRIPTION OF THE INVENTION

As used herein, all parts and percentages are by weight and all temperatures are in Centigrade, unless otherwise specified.

The nitrilotriacetonitrile to be used to produce the reaction mixture can be produced by any process, such as by reaction of ammonia or an ammonium salt with formaldehyde and hydrogen cyanide or by reaction of hexamethylenetetramine, formaldehyde, and hydrogen cyanide. It is preferred that nitrilotriacetonitrile be in the form of a crystalline solid. The concentration of nitrilotriacetonitrile in the reaction mixture is preferably from about 12% to about 30%, and even more preferably from about 16% to about 26%.

Any alkali metal hydroxide can be used to produce the corresponding salt of nitrilotriacetate. Preferred are sodium and potassium hydroxide and particularly preferred is sodium hydroxide. The alkali metal hydroxide and nitrilotriacetonitrile should be present in substantially stoichiometric amounts, which is meant to include reaction mixtures in which the molar ratio of alkali metal hydroxide to nitrilotriacetonitrile is from about 2.90 to about 3.10, preferably from about 2.95 to about 3.05, and most preferably about 3.03. The prior art has taught that use of substoichiometric amounts of hydroxide results in a highly colored, unsuitable product. However, using the process of this invention allows use of somewhat less than stoichiometric amounts of alkali metal hydroxide, without producing unacceptable color levels.

Partial hydrolysis of the reaction mixture takes place from about 25° C. to about 85° C., preferably from about 40° C. to about 70° C., and most preferably, about 60° C. Partial hydrolysis within this temperature range produces a soluble mixture of alkali metal salts of N-acetamide iminodiacetic acid and nitrilotriacetic acid. Once the nitrilotriacetonitrile has all been converted to this soluble mixture, the reaction is completed by boiling the mixture. Alternatively, after the nitrilotriacetonitrile has all been converted to soluble components, the reaction mixture may be held for a short time prior to boiling.

The hydrolysis reaction is completed by heating the reaction mixture to boiling, for at least 30 minutes, preferably at least about 60 minutes. During this boiling step, the ammonia evolved during the hydrolysis reaction is stripped from the reaction mixture. If necessary, additional ammonia stripping can be done by conventional means either before or after the boiling step. The boiling step may also be used to concentrate the product to aid in recovery of the crystalline nitrilotriacetate salt, or to produce a solution of a desired concentration. If further adjustment in concentration is desired, it can be accomplished by conventional means.

Any free cyanide can be removed from the reaction mixture by addition of an appropriate amount of formaldehyde.

In order to produce a product of acceptable color, at least about 0.04%, preferably about 0.04% to about 1.0%, more preferably about 0.1% to about 0.5%, and most preferably, about 0.2% of a bleaching agent is added to the reaction mixture. The bleaching agent is typically hydrogen peroxide, which can be added as an aqueous solution, usually 30–37% hydrogen peroxide.

However, any bleaching agent can be used, provided it does not cause decomposition or other reaction of the nitrilotriacetate salt product. Some examples are peracetic acid, peroxymonosulfuric acid, and others. The bleaching agent must be added after completion of the hydrolysis in the boiling step. If the bleaching agent is added prior to completion of the hydrolysis reaction, color development is actually enhanced.

If crystalline nitrilotriacetate salt is the desired product, it can be recovered by conventional means. Spray drying is the preferred means of recovering a crystalline product. The reaction mixture should contain about 40% to about 75% solids and preferably about 65% to about 75% solids, and most preferably about 70% solids, for best results on spray drying. The spray drying can be accomplished using conventional equipment.

If a solution of the nitrilotriacetate salt is the desired product, it can be produced by dissolving an appropriate amount of crystalline nitrilotriacetate salt in water, or by adjusting the concentration of the reaction solution as desired. Normally, a solution will contain no more than about 40% by weight of nitrilotriacetate salt.

The following Examples illustrate this invention, but are not intended in any way to limit its scope.

EXAMPLE I

A series of experiments were done in which reaction mixtures with about 27.6% nitrilotriacetonitrile and a mole ratio of sodium hydroxide to nitrilotriacetonitrile of 3.03 were partially hydrolyzed at various temperatures. The partial hydrolysis continued until all of the nitrilotriacetonitrile tonitrile (NTAN) went into solution. Hydrolysis at 60° C. was done for 60 minutes, and at 70° C. and 80° C. for 40 minutes. After the partial hydrolysis, one portion of the reaction mixture was analyzed by nuclear magnetic resonance spectroscopy (NMR) to determine the percentage of nitrilotriacetonitrile that had been converted to trisodium nitrilotriacetate (NTA) and to the sodium salt of N-acetamide iminodiacetic acid (ADA). A second portion was boiled about 60 minutes to complete the reaction and evaporated to dryness at about 120° C. This dry product was dissolved in water to form a 40% solution, and APHA color was determined. The results are shown on Table I.

| Temp. | Time NTAN All Soluble | % Converted to NTA | % Converted to ADA | APHA Color |
|---|---|---|---|---|
| 50° C. | 85 Min. | 63 | 37 | 85 |
| 55° C. | 61 Min. | 56 | 44 | 90 |
| 60° C. | 46 Min. | 59 | 41 | 50 |
| 70° C. | 26 Min. | 72 | 38 | 200+ |
| 80° C. | — | — | — | 200+ |

EXAMPLE II

A series of experiments were done in which a reaction mixture with about 22% nitrilotriacetonitrile and various mole ratios of sodium hydroxide to nitrilotriacetonitrile (NTAN), were partially hydrolyzed at about 60° C. for about 60 minutes. A portion of the reaction mixture was then analyzed by NMR to determine the percentage of nitrilotriacetonitrile that had been converted to trisodium nitrilotriacetate (NTA) and to the sodium salt of N-acetamide iminodiacetic acid (ADA). A portion was boiled for about 60 minutes and crystalline product was recovered by evaporation to dryness in a forced draft oven. The crystalline product was dissolved in water to form a 40% solution. The color of this solution was observed. The results of this series of experiments are shown in Table 2.

TABLE 2

| NTAN/NaOH Mole ratio | % Converted to NTA | % Converted to ADA | Color |
|---|---|---|---|
| 2.97 | 74 | 26 | slightly yellow |
| 2.94 | 88 | 12 | slightly yellow |
| 2.91 | 72 | 28 | slightly yellow |

The slightly yellow product solution was bleachable with 0.2% of 30% hydrogen peroxide at room temperature.

EXAMPLE III

A series of experiments was done in which a reaction mixture containing 14.2%, 21.6% and 27.9% nitrilotriacetonitrile and a mole ratio of sodium hydroxide to nitrilotriacetonitrile of 3.03 were partially hydrolyzed. The reaction mixture with 27.9% to nitrilotriacetonitrile was hydrolyzed for about 90 minutes, and the other two for about 60 minutes. The concentration of the reaction mixture with 27.9% nitrilotriacetonitrile exceeded solubility at all temperatures. The time at which all of the nitrilotriacetonitrile went into solution for the other two samples was noted. After the partial hydrolysis, the procedure used was similar to Example I. The results are shown in Table 3.

TABLE 3

| | 50° C. NTAN- All APHA | | 55° C. NTAN- All APHA | | 60° C. NTAN- All APHA | |
|---|---|---|---|---|---|---|
| % NTAN | soluble | Color | Soluble | Color | Soluble | Color |
| 14.2 | 23 min | Brown | 18 min | 200+ | 13 min | 200+ |
| 21.6 | 85 | 85 | 61 | 90 | 46 | 50 |
| 27.9 | — | 200 | — | 200 | — | 200 |

EXAMPLE IV

An apparatus was constructed to carry out the partial hydrolysis in a continuous manner. Partial hydrolysis was carried out in two flasks connected in series. Both flasks were maintained at about 60° C. The reaction mixture was a slurry with about 21.6% nitrilotriacetonitrile and with a mole ratio of sodium hydroxide to nitrilotriacetonitrile of about 3.03. The reaction mixture was fed into the first flask at a rate resulting in the average sojourn times in each of the flasks shown in Table 4. The partially hydrolyzed reaction mixture was withdrawn from the second flask and the partially hydrolyzed reaction mixture was stored below 60° C. Thereafter, the reaction mixtue was boiled for about 60 minutes and treated with 0.06% H2 O2 and 0.016% formaldehyde, to remove any remaining hydrogen cyanide. And the product was dried to the monohydrate. The dried product was dissolved in water to form a 40% solution, and APHA color was determined. The results are shown in Table 4.

TABLE 4

| Sojourn Time, per reactor | Temperature °C. | APHA Color |
|---|---|---|
| 57.0 minutes | 60° ± 2 | <10 |
| 59.4 | 60° ± 2 | <10 |

EXAMPLE V

To demonstrate the criticality of the time of addition of hydrogen peroxide, a slurry of about 21.6% nitrilotriacetonitrile and a mole ratio of sodium hydroxide to nitrilotriacetonitrile of about 3.03 was partially hydrolyzed at about 60° C. for about 60 minutes. This reaction product was split into 4 portions and treated as indicated. The dried product was dissolved in water to form a 40% solution. APHA color of this 40% solution was determined. The procedure and results are reported in Table 5.

TABLE 5

| Sample preparation | APHA color* |
|---|---|
| A. boiled about 60 minutes, then dried in 110° oven | 150 |
| B. boiled about 60 minutes, then bleached with 0.06% $H_2O_2$, then boiled, then dried in 110° oven | 90 |
| C. bleached for 16 hours at 25° C. with 0.06% $H_2O_2$, then boiled about 60 minutes, then dried in 110° C. oven | 150 |
| D. mixed with 0.06% $H_2O_2$, then dried in 110° C. oven | 400 |

*approximately 10 APHA color units are attributable to dissolved ferric compounds contaminating the sample.

If the hydrogen peroxide is added prior to boiling to complete the reaction, the APHA color of the product increases dramatically. This is believed to result from reaction between the hydrogen peroxide and N-acetamide iminodiacetic acid, or other hydrolysis intermediates. On the other hand, the APHA color is decreased markedly, if the partially hydrolyzed mixture is boiled to complete hydrolysis, prior to addition of the hydrogen peroxide.

I claim:

1. A process for producing a nitrilotriacetate salt, comprising:
   a. partially hydrolyzing a mixture of substantially stoichiometric amounts of nitrilotriacetonitrile and an alkali metal hydroxide in water at a temperature from about 25° C. to about 85° C.
   b. boiling said partially hydrolyzed mixture for at least about 30 minutes;
   c. adding at least about 0.04%, by weight of the mixture, of a bleaching agent which is non-reactive with the nitrilotriacetate salt product; and
   d. recovering a product 2. The process of claim 1 wherein the product recovered is crystalline nitrilotriacetate salt.

3. The process of claim 2, wherein said partial hydrolysis occurs from about 40° C. to about 70° C.

4. The process of claim 2, wherein said bleaching agent is from about 0.04% to about 1.0% by weight of the mixture.

5. The process of claim 2 wherein said bleaching agent is hydrogen peroxide.

6. The process of claim 2 wherein said crystalline nitrilotriacetate salt is recovered by spray drying the reaction mixture.

7. The process of claim 2 wherein said crystalline nitrilotriacetate salt is recovered by crystallization and filtration of the mixture.

8. The process of claim 2 wherein said partially hydrolyzed mixture is boiled for at least about 60 minutes.

9. The process of claim 2 wherein said alkali metal hydroxide is sodium hydroxide.

10. The process of claim 2 wherein said alkali metal hydroxide is potassium hydroxide.

11. A process for producing a crystalline nitrilotriacetate salt, comprising:
    a. partially hydrolyzing a mixture of an alkali metal hydroxide and nitrilotriacetonitrile, with a mole ratio from about 2.95 to about 3.05, in water at a temperature from about 40° C. to about 70° C., until all of the nitrilotriacetonitrile has been converted to soluble components;
    b. boiling said partially hydrolyzed mixture for at least about 30 minutes;
    c. adding from about 0.04% to about 1.0%, by weight of the mixture, of hydrogen peroxide; and
    d. recovering said crystalline nitrilotriacetate salt.

12. A process for producing crystalline trisodium nitrilotriacetate, comprising:
    a. partially hydrolyzing a mixture of sodium hydroxide and nitrilotriacetonitrile, with a mole ratio of from about 2.95 to about 3.05, in water at a temperature about 60° C. until all of the nitrilootriacetonitrile has been converted to soluble components;
    b. boiling said partially hydrolyzed mixture for at least about 60 minutes;
    c. adding from about 0.04% to about 1.0%, by weight of the mixture, of hydrogen peroxide; and
    d. spray drying the mixture to produce crystalline trisodium nitrilotriacetate.

13. The process of claim 1, wherein the product recovered is a solution of the nitrilotriacetate salt in water.

14. The process of claim 13, wherein said solution of nitrilotriacetate salt in water contains no more than about 40% by weight of nitrilotriacetate salt.

15. The process of claim 13, wherein said partial hydrolysis occurs from about 40° C. to about 70° C.

16. The process of claim 13, wherein said bleaching agent is from about 0.04% to about 1.0% by weight of the mixture.

17. The process of claim 13 wherein said bleaching agent is hydrogen peroxide.

18. The process of claim 13 wherein said partially hydrolyzed mixture is boiled for at least about 60 minutes.

19. The process of claim 13 wherein said alkali metal hydroxide is sodium hydroxide.

20. The process of claim 13 wherein said alkali metal hydroxide is potassium hydroxide.

21. A process for producing a solution of a nitrilotriacetate salt in water, comprising:
    a. partially hydrolyzing a mixture of an alkali metal hydroxide and nitrilotriacetonitrile, with a mole ratio from about 2.95 to about 3.05, in water at a temperature from about 40° C. to about 70° C., until all of the nitrilotriacetonitrile has been converted to soluble components;
    b. boiling said partially hydrolyzed mixture for at least about 30 minutes;
    c. adding from about 0.04% to about 1.0% by weight of the mixture, of hydrogen peroxide; and
    d. adjusting the concentration of the mixture.

22. A process for producing a solution of trisodium nitrilotriacetate in water, comprising:
    a. partially hydrolyzing a mixture of sodium hydroxide and nitrilotriacetonitrile, with a mole ratio from about 2.95 to about 3.05, in water at a temperature of about 60° C., until all of the nitrilotriacetonitrile has been converted to soluble components;

b. boiling said partially hydrolyzed mixture for at least about 60 minutes;

c. adding from about 0.04% to about 1.0% by weight of the mixture of hydrogen peroxide; and d. adjusting the concentration of said mixture to produce a solution with about 40% by weight of trisodium nitrilotriacetate.

* * * * *

UNITED STATES PATENT AND TRADEMARK OFFICE
CERTIFICATE OF CORRECTION

PATENT NO. : 4,547,589
DATED : October 15, 1985
INVENTOR(S) : Chung Y. Shen

It is certified that error appears in the above-identified patent and that said Letters Patent is hereby corrected as shown below:

In column 3, line 32, after the word "nitrilotriacetonitrile" delete the word "tonitrile".

In column 6, line 63, after the word "mixture" add "to the desired level".

Signed and Sealed this

Twentieth Day of May 1986

[SEAL]

Attest:

DONALD J. QUIGG

Attesting Officer

Commissioner of Patents and Trademarks